United States Patent
Mentak

(10) Patent No.: US 8,455,572 B2
(45) Date of Patent: Jun. 4, 2013

(54) METHOD OF MAKING OPHTHALMIC DEVICES AND COMPONENTS THEREOF FROM HYDROPHOBIC ACRYLIC (HA) POLYMERS WITH REDUCED OR ELIMINATED GLISTENINGS

(75) Inventor: Khalid Mentak, San Ramon, CA (US)

(73) Assignee: Key Medical Technologies, Inc., San Ramon, CA (US)

( * ) Notice: Subject to any disclaimer, the term of this patent is extended or adjusted under 35 U.S.C. 154(b) by 121 days.

(21) Appl. No.: 13/017,093

(22) Filed: Jan. 31, 2011

(65) Prior Publication Data

US 2012/0196951 A1    Aug. 2, 2012

(51) Int. Cl.
- C08J 3/24    (2006.01)
- G02B 1/04    (2006.01)
- C08F 4/04    (2006.01)
- C08F 4/34    (2006.01)

(52) U.S. Cl.
USPC ............ 523/344; 526/219.6; 526/230.5; 523/105; 264/1.32; 424/427; 525/376; 525/387

(58) Field of Classification Search
USPC ..... 523/105, 344; 526/219.6, 230.5; 264/1.32
See application file for complete search history.

(56) References Cited

U.S. PATENT DOCUMENTS

| | | | | |
|---|---|---|---|---|
| 3,222,426 | A | * | 12/1965 | Dietrich et al. ............... 525/257 |
| 4,328,329 | A | * | 5/1982 | Novak ....................... 526/219.2 |
| 4,607,087 | A | | 8/1986 | Moriya et al. |
| 5,470,932 | A | * | 11/1995 | Jinkerson ..................... 526/312 |
| 6,281,319 | B1 | | 8/2001 | Mentak |
| 6,313,187 | B2 | * | 11/2001 | LeBoeuf et al. ................ 522/13 |
| 6,635,731 | B2 | | 10/2003 | Mentak |
| 6,635,732 | B2 | | 10/2003 | Mentak |
| 7,083,645 | B2 | | 8/2006 | Mentak |
| 7,247,689 | B2 | * | 7/2007 | Makker et al. ................ 526/245 |
| 7,399,811 | B2 | | 7/2008 | Mentak et al. |
| 7,789,509 | B2 | | 9/2010 | Mentak et al. |
| 2004/0056371 | A1 | | 3/2004 | Liao et al. |
| 2009/0088493 | A1 | | 4/2009 | Laredo et al. |
| 2009/0281209 | A1 | | 11/2009 | Lehman et al. |
| 2010/0261858 | A1 | | 10/2010 | Mentak et al. |
| 2011/0021733 | A1 | | 1/2011 | Wanders et al. |

FOREIGN PATENT DOCUMENTS

| | | | |
|---|---|---|---|
| JP | 402051458 A | * | 2/1990 |
| JP | 403188111 A | * | 8/1991 |

OTHER PUBLICATIONS

Peter R. Dluzneski, "The chemistry of peroxide vulcanization", Rubber World, 0035-9572, Aug. 1, 2001.
Product Spec Sheet, "Diacyl Peroxides", Arkema Inc., 2006.
"Reimbursement guide Acrysof Toric Intraocular Lens", Arent Fox LLP, Feb. 2007.
International Search Report mailed Jul. 30, 2012 for PCT App. No. PCT/US2012/021690.

* cited by examiner

*Primary Examiner* — Tae H Yoon
(74) *Attorney, Agent, or Firm* — Whyte Hirschboeck Dudek S.C.; Grady J. Frenchick

(57) ABSTRACT

This invention relates to the fields of polymer chemistry, materials science and ophthalmology. More particularly it relates to optical components and method(s) of preparing same from hydrophobic acrylic (HA) monomer(s) that exhibit reduced or eliminated glistenings when implanted in a patient's eye. The method of this invention uses a mixture of one or more low temperature initiators (LTI) combined with one or more high temperature initiators (HTI), to polymerize one or more HA monomers to produce an optical HA polymer which, when used to manufacture an optical component and implanted as with an intraocular lens (IOL), exhibit reduced glistenings to the patient.

13 Claims, No Drawings

METHOD OF MAKING OPHTHALMIC DEVICES AND COMPONENTS THEREOF FROM HYDROPHOBIC ACRYLIC (HA) POLYMERS WITH REDUCED OR ELIMINATED GLISTENINGS

FIELD OF THE INVENTION

This invention relates to the fields of polymer chemistry, materials science and ophthalmology. More particularly it relates to an intraocular lens and method of preparing same that exhibits reduce or no glistenings when implanted in a patient's eye.

BACKGROUND

The following is provided as background solely for the benefit of the reader and is not intended, nor is it to be construed, as prior art to the present invention.

The intraocular lens ("IOL"), which can be surgically implanted in the eye of a patient, has experienced a remarkable history of innovation, each predicated on perceived shortcomings of its predecessor. For instance, the first rigid polymethylmethacrylate (PMMA) lens implanted in the posterior chamber between the iris and the lens by Harold Ridley in 1950 resulted in some relatively serious complications such as decentration or delocalization of the lens due to its size and weight and the frequent occurrence of uveitis.

In 1953, a few short years after the introduction of the Ridley lens, anterior chamber, the space between the cornea and the iris, implantable lenses were brought to market. These were held in place in the anterior chamber by a closed loop, which, as the name suggests, comprised a string-like piece of non-optic polymeric material attached at both ends to the lens proper, thus forming a loop. The early closed loops, like the lens itself, were rigid. Unfortunately, these lenses, due to their instability in the anterior capsule, were as prone to complications as the Ridley lens with bullous keratopathy, cystoid macular edema and glaucoma being the more common complications observed.

To correct instability, anterior chamber lenses were developed that relied on the papillary portion of the iris for anatomical fixation. Some lens designs required suturing to the iris, some clipped on. This, however, was found to lead to luxation of the lens when the pupil dilated unexpectedly. In about 1970, the anterior lens was again restructured, this time using a flexible closed-loop construct. Corneal damage, however, continued to be a problem and corneal transplants due to implant-related damage to the cornea were not uncommon.

The next innovation in the intraocular lens industry was the flexible open loop anterior chamber lens. As suggested by the name, "open loop" refers to a non-optic peripheral appendage that is attached to the lens proper at only one point, the other end of the loop being free to move about and conform to the surface of the eye. This resolved for the most part the corneal problems associated with intraocular lenses but other complications such as cystoid macular edema continued to occur.

In about 1975, the posterior chamber lens was introduced. As mentioned previously, the posterior chamber is the space behind the iris and in front of the eye's natural lens. While the optic portion of this lens, like its predecessors, was made of PMMA, its haptics, that is, the non-optic portion of the lens at the periphery used to hold the lens in place as exemplified by the closed and open loop configurations noted above were often made of such materials as polyamide or polypropylene. While these lenses offered numerous advantages such as fewer corneal problems, less retinal detachment and less uveitis-glaucoma-hyphaema (UGH) syndrome, they still required relatively large incisions, approaching 6 mm in length, for implantation. Driven by the advent of phacoemulsion technology for the removal of lenses clouded by cataracts through very small incisions to the eye, foldable intraocular lenses were developed. These lenses can be folded to fit through the same incision used to remove the natural lens i.e., as small as 2.5-3.0 mm, and then unfolded to operational size once within the eye.

One of the predominant types of foldable intraocular lenses presently in use is the so-called hydrophobic acrylic lens (hereafter sometimes referenced as an "HA lens") as exemplified by the Alcon Acrysof® and AcryS of Toric® lens. These lenses, while relatively new in ophthalmology, seem to be avoiding many, if not most, of the complications of their predecessors.

A problem has arisen with the hydrophobic acrylic lenses, however. The lenses, when implanted in a patient's eye, tend, over time, to form small, light reflective regions in their structure called "glistenings." While the actual cause of glistenings remains unresolved, one theory is that even though these lenses are nominally hydrophobic, over time some water is able to enter into vacuoles in the polymeric matrix comprising the lens thereby changing the refractive index of the lens of those points, which change appears as reflective spots or "glistenings." While there is still some debate over the effect of glistenings at the clinical level, there remains a concern that in worse case scenarios a loss of visual acuity might occur that may require excision of the lens. Even at lesser levels, glistenings can cause glare and other annoyances to patients who have implanted hydrophobic intraocular lenses.

Thus, there is a need for an HA foldable intraocular lens that either is not susceptible to glistenings at all or has a substantially reduced tendency to form glistenings. The present invention provides such a lens.

BRIEF SUMMARY OF THE INVENTION

Briefly, in one aspect, the current invention relates to methods for making optical components, e.g., intraocular lenses, comprising an optical hydrophobic acrylic (HA) polymer or HA polymer blend, and to lenses thereby made. Specifically, a method of present invention is for making an optical component of an ophthalmic device (including a completed device) from an HA polymer, the device thus made having reduced glistenings as perceived by a user of the device. The method comprising the steps of:
  providing a monomer or a mixture of monomers which, when polymerized produce a hydrophobic acrylic polymer which can be formed into an optical component of an ophthalmic device;
  providing two or more polymerization initiators, one of the initiators being a low temperature initiator (LTI), the other polymerization initiator being a high temperature initiator (HTI);
  combining the initiators with the hydrophobic acrylic monomer(s) to create a reaction mixture;
  reacting the reaction mixture to produce a hydrophobic acrylic polymer; and
  forming the polymer into the optical component.

In a preferred practice of this method the "reacting" step includes the steps of:
  exposing the reaction mixture to a temperature of 50° C. for 1 to 4 hours;
  exposing the reaction mixture to a temperature of 60° C. for a time period of 1 to 6 hours; and exposing the reaction mixture to a temperature of 100° C. for from about 1 to 12 hours.

Generally these step-wise increases in exposing, curing or reacting temperatures will take place in the order indicated.

Optical components, assemblies and subassemblies made from HA polymers made according to the above-noted method are another aspect of this invention.

In an aspect of this invention, the intraocular lens is a foldable intraocular lens. Several methods were used in the past to reduce glistenings in HA polymers including incorporating hydrophobic monomers e.g., U.S. Pat. No. 7,789,509 to Mentak, U.S. Pat. No. 6,281,319 to Mentak, U.S. Pat. No. 6,635,731 to Mentak, U.S. Pat. No. 6,635,732 to Mentak, and U.S. Pat. No. 7,083,645 to Mentak, hydration e.g., U.S. Pat. No. 7,789,509 to Mentak et al., and formation of nanodomains e.g., U.S. Pat. No. 7,399,811 also to Mentak et al. All of the previously listed patents are incorporated by reference herein. However, prior methods require changing the chemical composition of the base polymer or storing the lenses in saline or water, thereby reducing the refractive index (RI) of the polymer and limiting the use of packaging option such as preloading invention.

The current method teaches a novel approach to reducing or eliminating patient-perceived glistening in HA polymer optical components without altering the chemical composition of the base polymer or the need to hydrate the lenses. In addition, this method allows improved control over the softness of the material reflected by its so-called glass transition temperature (Tg). Thus, there is a need for an acrylic foldable intraocular lens, particularly a hydrophobic acrylic foldable IOL, that either is not susceptible to glistenings at all or has a substantially reduced tendency to form glistenings. The present invention provides such a lens.

HA polymers are usually made via free radical polymerization of vinyl monomers using free radical initiators. A single initiator (e.g. AIBN) is usually used to create free radical and allow copolymerization to proceed. This may cause invisible micro defects to form during various stages of the polymerization process. Such micro defects allow an uneven water sorption and subsequent glistenings formation when the lenses are implanted. We have recently discovered that if the polymerization rate is controlled during various stages of the manufacturing process so as to reduce micro defects the formation of glistenings in HA IOLS is greatly reduced or eliminated. This is achieved by using two or more free radical initiators; a low temperature initiator (LTI) and a higher temperature one (HTI). An LTI is defined as having a 10 hour half-life temperature of about 61° C. or less. A HTI is defined as having a 10 hour half-life temperature of about 62° C. or greater. It is preferable that the ΔTI is about 10° C. or more. Generally speaking the temperature difference in the 10 hour half-life temperature of the LTI from the HTI i.e., (ΔTI) should be at least 5° C., preferably 15° C. and most preferably 25° C. It is preferable that the ΔTI is about 10° C. or more. As a further general matter, the total initiator concentration (% LTI and % HTI) should be about 0.05 wt %. to 2 wt. %, preferably about 1 wt % of the reaction mixture prior to polymerization. The ratio of LIT:HTI should be about 1:10 to 10:1, preferably about 1:3 to 3:1 and most preferably about 1:1.

The term "ten hour half-life temperature" is used extensively herein in reference to the selection of polymerization initiators. As is well known to those of skill in the polymer art the ten hour half-life temperature of a particular initiator is a measure of its stability. It is specifically the temperature of an initiator at which 10 hours is the time needed to decompose 50% of the initiator sample. Initiator decomposition prompts monomer polymerization. The higher the ten hour half-life temperature of a particular initiator the more stable it is, and the more slowly polymerization (including chain extension and cross-linking) proceeds at any given temperature. Conversely the lower the ten hour half-life temperature of an initiator the more quickly the polymerization reaction proceeds at any given temperature.

The surprising and unexpected reduction in glistenings found in optical components produced in practice of this invention is due to the selection and use of the LTIs and HTIs herein noted, to provide polymerization reaction rate control. See U.S. Pat. No. 4,607,087 to Moriya et al. which is also incorporated by referenced herein.

Table 1 below lists some useful initiators and their 10 HR Half-life Temps.:

| LTIs | Chemical Name | Solvent | 10 HR Half-life Temp. (° C.) |
| --- | --- | --- | --- |
| Luperox 610 | 3-hydroxy-1,1-dimethylbutyl peroxyneodecanoate | trichloroethylene | 37 |
| Luperox 188 | a-cumyl peroxyneodecanoate | trichloroethylene | 38 |
| Luperox 688 | 2-hydroxy-1,1-dimethylbutyl peroxyneoheptanoate | alpha-methylstyrene | 41 |
| Luperox 288 | a-cumyl peroxyneoheptanoate | trichloroethylene | 43 |
| Luperox 546 | t-amyl peroxyneodecanoate | trichloroethylene | 46 |
| Luperox 10 | t-butyl peroxyneodecanoate | trichloroethylene | 48 |
| Luperox 223 | di(2-ethylhexyl) peroxydicarbonate | trichloroethylene | 49 |
| Luperox 221 | di(n-propyl) peroxydicarbonate | trichloroethylene | 50 |
| Luperox 225 | di(sec-butyl) peroxydicarbonate | trichloroethylene | 51 |
| Luperox 701 | t-butyl peroxyneoheptanoate | trichloroethylene | 53 |
| Luperox 554 | t-amyl peroxypivalate | trichloroethylene | 55 |
| Luperox 11 | t-butyl peroxypivalate | trichloroethylene | 58 |
| Luperox 219 | diisononanoyl peroxide | trichloroethylene | 61 |

| HTIs | Chemical Name | Solvent | 10-HR-Half-life Temp. (° C.) |
| --- | --- | --- | --- |
| Luperox LP | didodecanoyl peroxide | trichloroethylene | 64 |
| Luperox 665 | 3-hydroxy-1,1-dimethylbutylperoxy-2-ethylhexanoate | alpha-methylstyrene | 65 |
| Luperox DEC | didecanoyl peroxide | trichloroethylene | 65 |
| AIBN | 2,2'-azobis(isobutyronitrile) | toluene | 65 |
| Luperox SAP | di(3-carboxypropionyl) peroxide | acetone | 66 |

-continued

| | | | |
|---|---|---|---|
| Luperox 256 | 2,5-dimethyl-2,5-di(2-ethylhexanoylperoxy)hexane | decane | 73 |
| Luperox A | dibenzoyl peroxide | benzene | 73 |
| Luperox 575 | t-amylperoxy 2-ethylhexanoate | dodecane | 75 |
| Luperox 26 | t-butylperoxy 2-ethylhexanoate | dodecane | 77 |
| Luperox 80 | t-butyl peroxyisobutyrate | decane | 82 |
| Luperox PMA | t-butyl peroxy-(cis-3-carboxy)propenoate | acetone | 87 |
| Luperox 531 | 1,1-di(t-amylperoxy)cyclohexane | dodecane | 93 |
| Luperox 231 | 1,1-di(t-butylperoxy)-3,3,5-trimethylcyclohexane | dodecane | 96 |
| Luperox 331 | 1,1-di(t-butylperoxy)cyclohexane | dodecane | 97 |
| Luperox TAEC | OO-t-amyl O-(2-ethylhexyl) monoperoxycarbonate | dodecane | 99 |
| Luperox TBIC | OO-t-butyl O-isopropyl monoperoxycarbonate | benzene | 99 |
| Luperox TBEC | OO-t-butyl O-(2-ethylhexyl) monoperoxycarbonate | dodecane | 100 |
| Luperox JW | polyether tetrakis(t-butylperoxycarbonate) | ethylbenzene | 100 |
| Luperox 118 | 2,5-dimethyl-2,5-di(benzoylperoxy)hexane | benzene | 100 |
| Luperox 555 | t-amyl peroxyacetate | dodecane | 100 |
| Luperox TAP | t-amyl peroxybenzoate | dodecane | 100 |
| Luperox 270 | t-Butyl Peroxyisononanoate | benzene | 101 |
| Luperox 7 | t-butyl peroxyacetate | decane | 102 |
| Luperox P | t-butyl peroxybenzoate | dodecane | 104 |
| Luperox KDB | di-t-butyl diperoxyphthalate | benzene | 104 |
| Luperox 220 | 2,2-di(t-butylperoxy)butane | dodecane | 107 |
| Luperox 553 | 2,2-di(t-amylperoxy)propane | dodecane | 108 |
| Luperox 230 | n-butyl 4,4-di(t-butylperoxy)valerate | dodecane | 109 |
| Luperox 533 | ethyl 3,3-di(t-amylperoxy)butyrate | dodecane | 112 |
| Luperox 233 | ethyl 3,3-di(t-butylperoxy)butyrate | dodecane | 114 |
| Luperox DC | dicumyl peroxide | decane | 117 |
| Luperox F | a,a'-bis(t-butylperoxy)diisopropylbenzene | dodecane | 119 |
| Luperox 101 | 2,5-dimethyl-2,5-di(t-butylperoxy)hexane | dodecane | 120 |
| Luperox DTA | di(t-amyl) peroxide | dodecane | 123 |
| Luperox 801 | t-butyl a-cumyl peroxide | dodecane | 124 |
| Luperox DI | di(t-butyl) peroxide | decane | 129 |
| Luperox 130 | 2,5-dimethyl-2,5-di(t-butylperoxy)-3-hexyne | dodecane | 131 |

DETAILED DESCRIPTION OF THE INVENTION

As used herein, an "intraocular lens" refers to a polymeric phakic or aphakic (also referred to in the art as pseudophakic), vision-correcting device that may be implanted into a patient's eye. Phakic lenses are used to correct refractive errors such as myopia (near-sightedness), hyperopia (far-sightedness) and astigmatism (blurred vision due to poor light focusing on the retina due to an irregularly shaped cornea or, in some instances, an irregularly shaped natural lens). The natural lens remains in place when a phakic lens is implanted while the lens is removed prior to implantation of pseudophakic lens. An aphakic or pseudophakic lens is inserted in the eye subsequent to removal of the natural lens due to disease, most often a cataract; that is, clouding of the natural lens. Either type of lens may be implanted in the anterior chamber in front of the iris or in the posterior chamber behind the iris and in front of the natural lens or in the region where the natural lens was before removal. While intraocular lenses may be "hard," that is relatively inflexible, or "soft," i.e., relatively flexible but not foldable, for the purpose of this invention the presently preferred lens is a foldable acrylic polymer lens. A foldable lens is one that is sufficiently flexible that it can be folded into a smaller configuration to permit its implantation into the eye through a much smaller incision that is necessary for hard or soft lenses. That is, while hard and soft lenses may require a 6 mm or larger incision, a foldable lens usually requires only a 3 mm or even smaller incision.

As used herein, the terms "approximately," "essentially," "substantially," "about," "slightly" or any other term of approximation, unless otherwise expressly stated, mean±5% from the figure set forth.

As used herein, a "patient" refers to any sighted species suffering from a disorder related to visual acuity. In particular, a patient is a mammal, most particularly a human being. As used herein, a patient is "in need of" an intraocular lens when the patient's natural lens either passes light only partially or not at all as the result of opacification of the lens, or passes light, but does not properly focus it on the retina. Such may occur as the result of natural conditions, i.e., aging, or it may occur as a symptom of another disease such as, without limitation, diabetes.

As used herein, a "polymer" refers to a homopolymer prepared by the polymerization of a single monomer, or to a copolymer (or terpolymer, etc.) prepared by the polymerization of two or more different monomers. Copolymers may be random, alternating, ordered block, random block or graft copolymers. "hydrophobic" polymers herein have an equilibrium water content at approximately body temperature, i.e., about 37° C., from about 0 wt % to about 12 wt %, preferably from about 2 wt % to about 8 wt % and presently most preferably from about 3 wt % to about 6 wt %. Such polymers are generally referred to herein and by those of ordinary skill in the intraocular lens art as "hydrophobic polymers," even though they are capable of absorbing and retaining significant amounts of water.

As used herein, "optical polymer" refers to a polymer that is suitable for implantation into a patient's eye and that is capable of addressing ophthalmic conditions of the lens of the eye such as, without limitation, myopia, hyperopia, astigmatism and cataracts. In general such a polymer will be biocompatible, i.e., it will not cause any inflammatory, immunogenic, or toxic condition when implanted, it will form a clear, transparent, colorless (unless intentionally colored for a particular application) film-like membrane, and it will have a refractive index greater than about 1.4, preferably greater than about 1.5 and presently most preferably greater than about 1.55.

As used herein, "optical component", "optical assembly" or "optical subassembly" shall mean a portion of, or a completed, ophthalmic device, assembly or subassembly which in its normal utilization or use could or would generate "glistenings", as that term is used in this art, which would be seen or sensed by the user of the assembly or subassembly (e.g., a patent). Non-limiting examples of optical components include lens bodies, optic bodies, haptics; IOL components. Exemplary non-limiting optical components, including completed IOLs are shown at FIGS. 2(A) and 2(B); 3(A) and 3(B) and 4(A) and (4(B) of Patent Application Publication 2004/0056371 A1, those figures being incorporated by reference herein.

An intraocular lens of this invention may be produced as a step in the manufacturing process used to create the lens. For example, without limitation, a manufacturing process may include the steps of polymer synthesis, polymer sheet casting, button cutting, optic lathe cutting, optic milling, haptic attachment, polishing, solvent extraction, sterilization and packaging.

Exemplary embodiments for the hydrophobic acrylic ("HA") polymers used in the present invention include homopolymers and copolymers as well as their crosslinked counterparts with appropriate crosslinkers. Monomers suitable for the preparation of hydrophobic acrylic polymers cover a wide range of structures including, but not limited to: phenoxyethylacrylate, 2-phenylethylacrylate, styrene, methylacrylate, ethylacrylate, hexylmethacrylate, laurylmethacrylate, stearylacrylate, methylmethacrylate, phenoxyethylmethacrylate, 2-phenylethylmethacrylate, laurylmethacrylate, stearylmethacrylate, alkylacrylate derivatives and alkylmethacrylate derivatives.

Crosslinkers for the homopolymer of the present invention are selected from a wide group of diacrylates or dimethacrylates or a mixture thereof. However, they are preferably selected from those with a rigid structure group. The rigid group includes, but is not limited to, the structure of alkylaryl, biphenyl and naphthalene groups and other similar structures. Examples of crosslinkers containing a rigid group are: diacrylates and dimethacrylates of bisphenol A ethoxylate (1 EO/phenol), bisphenol A ethoxylate (2 EO/phenol), bisphenol A propoxylate (2 PO/phenol), bisphenol A, 2,2'-diallyl-bisphenol A, bis(4-(2-acryloylethoxy)phenyl)methane, bis(4-(2-methacryloylethoxy)phenyl)methane, bis(naphthol) A ethoxylate (X EO/naphthol), bis(2-acryloylalkylphenyl)propane, bis(2-methacryloylalkylphenyl)propane, 3,3'-(ethylenedioxy)diphenyl A ethoxylate (X EO/phenol), and naphthdiol A ethoxylate(2×EO/naphthalene), wherein X=1-5. For example, a mixture of 95% phenoxyethylacrylate and 5% of bisphenol A dimethacrylate with optional WV absorbers can be heated to about 45° C. in the presence of free radical initiator, such as azobisisobutyronitrile (AIBN). After the pre-polymer gelation process, IOLs can be made from this viscous gel and easily released from the fused silica mold.

Crosslinkers suitable for the copolymer in the present invention can be, in general, any difunctionally polymerizable molecule. Examples include, but are not limited to, ethyleneglycol diacrylate, ethyleneglycol dimethacrylate, 1,3-propanediol diacrylate, 1,3-propanediol dimethacrylate, 1,4-butanediol diacrylate, 1,4-butanediol dimethacrylate, 1,6-hexanediol diacrylate, 1,6-hexanediol dimethacrylate, allyl acrylate, allyl methacrylate, etc.

The hydrophobic acrylic polymer suitable for ophthalmic lenses in the present invention optionally includes a UV absorbing agent to block UV rays from entering the eye. Examples of suitable UV absorber agents include substances containing a benzophenol chromophore or benzotriazol chromophore. Specifically, the following chemicals can be used as a UV absorber: 2-(4-benzoyl-3-hydroxyphenoxy)ethyl acrylate, 2-hydroxy-4-allyloxybenzophenone, 2-(2'-hydroxy-5-acryloxyethylphenyl)-2H-benzotriazole, and 2-(2'-hydroxy-5-methacryloxyethylphenyl)-2H-benzotriaz-ole.

After an IOLs optic, lens, lens component, or lens blank is produced by polymerization of about one or more about HA monomers or HA monomer mixture it may be necessary to post-cure the IOL at an elevated temperature to complete the polymerization and crosslinking. However, many polymerization processes leave un-reacted monomers, non-active monomers, low molecular weight oligomers and other impurities in the cured IOL. These impurities should be removed as completely as possible to ensure lens clarity and biocompatibility, i.e., no leachable impurities once the lens is implanted in the eye.

Various extraction methods were tested for their feasibility. Lenses placed in isopropanol (EPA) in a flask were stirred for 3 days at 50° C. in a shaker with a fresh solvent at least once in every 24 hours. Alternatively, a standard Soxhlet extraction apparatus was also used for IOL extraction with various organic solvents. While alcoholic solvents generally performed with much better efficiency than alkanes, it appears that ethanol was a particularly effective solvent among all solvents tested. In addition, extraction time also played a significant role in minimizing the lens haziness or glistenings. Generally extraction takes place for at least about 24 hours; preferably the extraction time is in the range of from about 48 to about 72 hours.

Furthermore, drying conditions may play an important role in eliminating glistenings. It was found that a slow drying process is preferred with a long drying time, such as about 48 hours or more, and that the drying temperature needs to be lower than the boiling temperature of the solvent used for extraction. Faster drying processes may result in the formation of more glistenings in the finished lens.

EXAMPLES

Various copolymers are prepared by mixing the following ingredients under reduced pressure: comonomers, a crosslinker, and a polymerizable UV blocking agent. Vinyl benzotriazole or vinyl benzophenone at a total concentration of 0.1-1.0% by weight is utilized as UV blocking agents. Blue light blocking chromophores such as vinyl Orange 3 may also be added at a concentration of 0.01-0.1% by weight. To initiate polymerization the free radical initiator mixtures is employed at concentration of 0.05-0.6% by weight. The monomer solution is mixed in a glass flask using a magnetic stir bar for 30 minutes. The solution is then filtered through a 0.2 micron (µ) filter and injected into a sheet mold comprising two glass plates held together with spring clips and separated by a plastic gasket. The mold is then placed in a water bath for 4 hours at 50° C. followed by 6 hours at 60° C. then removed and post cured at 100° C. in oven for 12 hours. A clear, soft polymer sheet is obtained. A disk of 1 cm in diameter and 2 mm in thickness is cut from the sheet and polished. Glistenings evaluation is carried out by soaking disk samples in saline at 50° C. for 72 hours and then inspecting the samples at 20×. Glistenings are graded from a scale of 0 to 4. Table 2 below summarizes the results:

TABLE 2

| Example | Copolymer | RI | $T_g$ (°C.) | Glistenings Grade 0.2% AIBN | 0.1% AIBN/0.1% Luperox 10 | 0.1% AIBN/ 0.1% Luperox 221 |
|---|---|---|---|---|---|---|
| 1 | PEA-PEMA(80/20) | 1.5554 | 8 | 4 | 1 | 1 |
| 2 | PEA-PEMA(70/30) | 1.5555 | 11 | 4 | 1 | 0 |
| 3 | BA-BMA(90/10) | 1.5648 | 12 | 4 | 2 | 1 |
| 4 | BA-BMA(90/10) | 1.5627 | 16 | 4 | 1 | 1 |
| 5 | PNVC-PEA(10/90) | 1.5763 | 10 | 4 | 0 | 1 |
| 6 | PNVC-LM(30/70) | 1.5663 | 13 | 4 | 0 | 2 |
| 7 | PEMA-LM(60/40) | 1.5434 | 8 | 3 | 0 | 0 |

| Example | Copolymer | RI | $T_g$ (°C.) | 0.2% AIBN | 0.1% AIBN/0.1% Luperox 688 | 0.1% AIBN/ 0.1% Luperox 546 |
|---|---|---|---|---|---|---|
| 8 | PEA-PEMA(80/20) | 1.5554 | 8 | 4 | 2 | 0 |
| 9 | PEA-PEMA(70/30) | 1.5555 | 11 | 4 | 0 | 1 |
| 10 | BA-BMA(90/10) | 1.5648 | 12 | 4 | 1 | 1 |
| 11 | BA-BMA(90/10) | 1.5627 | 16 | 4 | 0 | 2 |
| 12 | PNVC-PEA(10/90) | 1.5763 | 10 | 4 | 1 | 0 |
| 13 | PNVC-LM(30/70) | 1.5663 | 13 | 4 | 0 | 1 |
| 14 | PEMA-LM(60/40) | 1.5434 | 8 | 3 | 1 | 0 |

PEA Phenyethyl acrylate
PEMA Phenyethyl methacrylate
BA Benzyl acrylate
BMA Benzyl methacrylate
PNVC Poly N-vinyl carbazole
LM Lauryl methacryalte
All samples contain 3% ethylene glycol dimethacrylate as crosslinker and 0.3% Cyasorb as UV absorber A further aspect of this invention is a method of reducing or eliminating glistenings produced and perceived by a patient in an intraocular lens comprising providing an intraocular lens comprising at least in part an HA polymer or HA polymer blend, the HA polymer produced in a polymerization process employing a combination of LTI and HTI initiators.

What is claimed is:

1. A method for making a hydrophobic acrylic (HA) optical component having reduced glistenings comprising the steps of:
   providing a monomer or a mixture of monomers which, when polymerized produce a hydrophobic acrylic polymer which can be formed into an optical component of an ophthalmic device;
   providing two or more polymerization initiators, one of the initiators being a low temperature initiator (LTI), the other polymerization initiator being a high temperature initiator (HTI);
   combining the initiators with the hydrophobic acrylic monomer(s) to create a reaction mixture;
   reacting the reaction mixture by the steps of:
   to produce a hydrophobic acrylic polymer; and
   exposing the reaction mixture to a temperature of 50° C. for 1 to 4 hours;
   exposing the reaction mixture to a temperature of 60° C. for a time period of 1 to 6 hours; and
   exposing the reaction mixture to a temperature of 100° C. for from about 1 to 12 hours to produce a hydrophobic acrylic polymer; and
   forming the polymer into the optical component.

2. A method according to claim 1 wherein the optical component is the optic of an intraocular lens.

3. A method according to claim 1 wherein the LTI has a 10 hour half-life temperature of 61° C. or lower.

4. A method according to claim 1 wherein the HTI has a 10 hour half-life temperature of 62° C. or higher.

5. A method according to claim 1 wherein the 10 hour half-life temperature difference below the LTI and the HTI is at least 5° C.

6. A method according to claim 1 wherein the 10 hour half-life temperature difference below the LTI and the HTI is at least 15° C.

7. A method according to claim 1 wherein the mixture of polymerization initiators is present in the range of about 0.05 to about 2.0 weight percent of the reaction mixture.

8. A method according to claim 1 wherein the reaction mixture is combined with about 0.1 to about 1.0 weight percent UV blocking agent before being reacted.

9. A method according to claim 1 wherein the reaction mixture is combined with about 0.1 to about 1.0 weight percent blue light blocking chromophore before being reacted.

10. A method according to claim 1 wherein the mixture of initiators comprises about 10 to about 90 weight percent LTI and concomitantly about 90 to about 10 weight percent HTI.

11. A method according to claim 1 wherein the LTI is di(n-propyl) peroxydicarbonate.

12. A method according to claim 1 wherein the HTI is 2.2'-azobis(isobutyronitrile).

13. A method according to claim 1 wherein the LTI is di(n-propyl) peroxydicarbonate and the HTI is 2.2'-azobis(isobutyronitrile).

* * * * *